Figure 1:
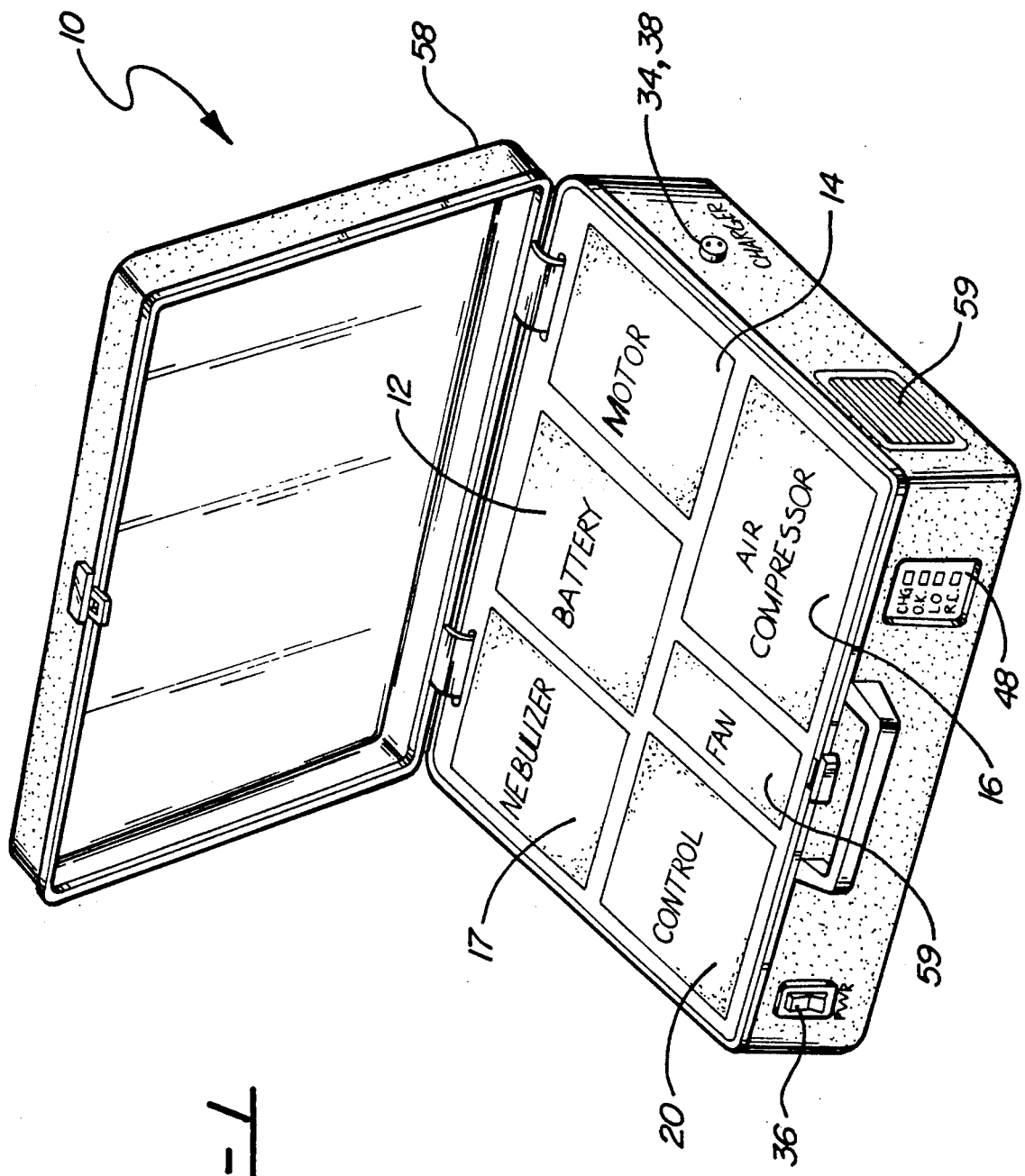
Figure 2:
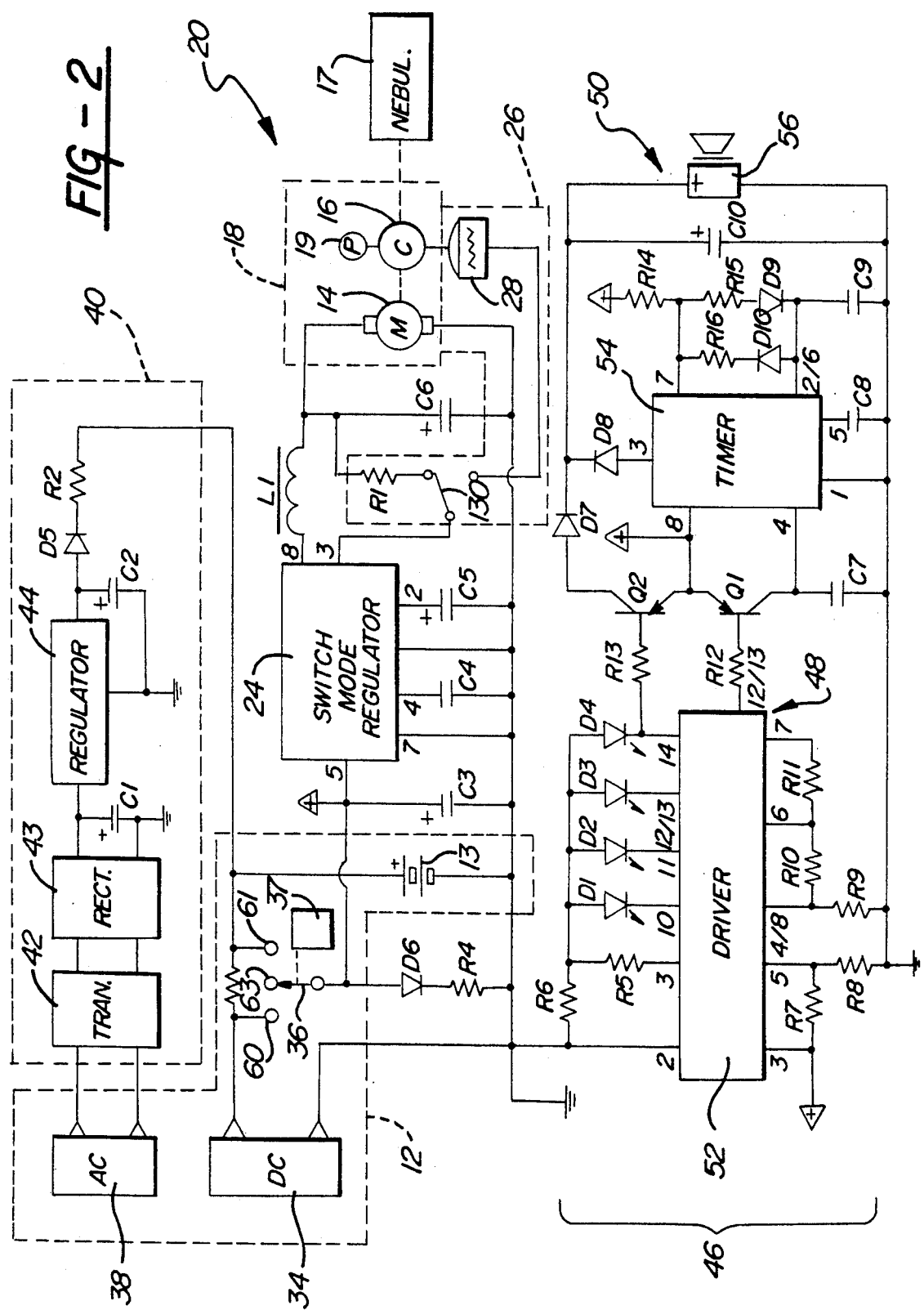

United States Patent [19]

Hochstein

[11] Patent Number: 5,022,587

[45] Date of Patent: Jun. 11, 1991

[54] BATTERY POWERED NEBULIZER

[76] Inventor: Peter A. Hochstein, 2966 River Valley Dr., Troy, Mich. 48098

[21] Appl. No.: 362,570

[22] Filed: Jun. 7, 1989

[51] Int. Cl.$^5$ ............................................. B67D 5/08
[52] U.S. Cl. ...................................... 239/72; 239/71; 239/338; 315/307
[58] Field of Search .................... 239/338, 72, 71, 63, 239/8; 128/200.18, 200.21, 200.22; 315/307

[56] References Cited

U.S. PATENT DOCUMENTS

| | | | |
|---|---|---|---|
| 4,146,049 | 3/1979 | Kruse et al. | 239/71 |
| 4,150,721 | 4/1979 | Norwood | 166/66 |
| 4,244,361 | 1/1981 | Neubert | 128/200.21 |
| 4,257,415 | 3/1981 | Rubin | 128/200.21 |
| 4,326,161 | 4/1982 | Kreinberg | 315/307 |
| 4,334,531 | 6/1982 | Reichl et al. | 239/338 |
| 4,383,951 | 5/1983 | Palson | 239/71 |
| 4,461,425 | 7/1984 | Miller | 239/338 |
| 4,634,294 | 1/1987 | Christol et al. | 340/600 |
| 4,743,831 | 5/1988 | Young | 340/636 |
| 4,836,452 | 6/1989 | Fox | 239/338 |

Primary Examiner—Andres Kashnikow
Assistant Examiner—Christopher G. Trainor
Attorney, Agent, or Firm—Reising, Ethington, Barnard, Perry & Milton

[57] ABSTRACT

A battery powered nebulizer (10) includes a portable housing (58) containing a battery power supply (13), pump-motor combination (14), air compressor (16) and control circuitry (20). The control circuitry (20) includes a pulse width modulator (24) for switching power to the motor (14) to conserve battery charge and regulate the pump-motor combination (14) to a predetermined volume output. The nebulizer (10) includes a charger (40) for charging the battery (13) and an adapter (34) to be connected to an external battery supply. A monitor (46) monitors the charge on the battery (13) to audibly and visually indicate low battery charge.

17 Claims, 2 Drawing Sheets

BATTERY POWERED NEBULIZER

TECHNICAL FIELD

The invention relates to nebulizers or fog generators used for humidification of ambient air, and more specifically, to the control of output volume of fog by the nebulizer.

BACKGROUND OF THE INVENTION

Nebulizers or fog generators are commonly used for humidification of ambient air and for inhalation therapy. Treatment of certain respiratory conditions, such as asthma, by this method is the preferred treatment. Generation of stable, micron-size aerosol fogs is commonly accomplished by either air driven nebulizers or by ultrasonic generators. Electronic equipment used for ultrasonic mist generation is relatively complex, cumbersome, and is hardly portable. Conventional air driven nebulizers are, small, rugged and low in cost and may be disposable. However, the ancillary air compressor is usually large and requires AC power to function. The diaphragm pumps could be converted to DC operation, but their relative in efficiency and the attendant high power drain would dictate a rather massive battery for reasonable running times.

Portable air compressors suitable for use with commercially available inhalation therapy nebulizers generally develop about 0.4 scfm at 12 to 13 psi. This pressure range is best served by efficient positive displacement, piston or rotary vane compressors driven by efficient permanent magnetic DC motors. Available nebulizers provide optimal performance in inhalation therapy over a relatively narrow range of pressure. In air compressor applications, changes in motor excitation voltage will naturally result in variations in the pressure-volume characteristics of the pump. Experiments have shown that relatively small, i.e., 10%, changes in voltage can adversely effect the efficiency of treatment when nebulizers are coupled to air compressors driven by DC motors. In situations where complete portability is desired, secondary or storage batteries must be used as a power source for such DC motor-compressor. Practical battery systems for such an application include nickel cadmium or sealed (gelled electrolyte) lead-acid cells. The requisite air pressures and volumes can be developed by small and efficient motor-pump combinations, but at best these consume over 36 watts of electrical power. Given a minimal treatment schedule of at least four 15 minute sessions for a portable nebulizer, battery capacity, size, weight and cost become critical factors.

For cost effective applications, sealed lead-acid batteries offer a good value, albeit with penalties in weight and package volume. However, the normal voltage decay characteristic of any storage battery system presents problems if a relatively long period of constant voltage is desired, particularly at high current, without having to resort to large, heavy batteries. Constant voltage is available only over a relatively small portion of the capacity curve.

SUMMARY OF THE INVENTION AND ADVANTAGES

The invention is a method of producing fog and a nebulizer assembly comprising power supply means for supplying power, generating means for producing fog, control means connected between the power supply means and the generating means for switching power to the generating means to produce a predetermined volume. The control means is characterized by including pulsing means for receiving the power and transmitting a series of pulses of power to the generating means to establish an average power producing the predetermined volume of fog.

The invention also includes power storage means for storing a charge and supplying power, generating means for receiving the power and producing fog, monitor means for monitoring the amount of charge in the power storage means and indicator means for indicating a low charge state.

An advantage of the invention is that using a pulsed controller, very efficient use of battery capacity is possible Use of such pulsing means also enables portability of the device by minimizing the size of the battery. Furthermore, the remaining charge on the battery is indicated to warn the user of a low battery charge. Such monitoring capability is important when requiring regular treatments.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a perspective view of the subject invention; and

FIG. 2 is a schematic diagram of the subject invention.

DESCRIPTION OF THE PREFERRED EMBODIMENT

A nebulizer assembly is generally shown at 10 in FIG. 1. The assembly 10 is portable and supplied power by a power supply means 12, preferably a battery 13. The assembly 10 produces fog or humidification of ambient air by generating means 18 comprising a motor-pump combination 14, air compressor 16, and air driven nebulizer 17 and pressure gage 19 as commonly known in the art.

The assembly 10 includes control means 20 connected between the power supply means 12 and the generating means 18 for switching power to the generating means 18 to control the volume of fog produced to a predetermined volume. The control means 20 switches power to the generating means 18 by a series of timed pulses, rather than supplying continuous power, in order to conserve battery 13 life and maintain the motor-pump combination 14 at a uniform speed thereby maintaining fog volume at the predetermined volume.

The control means 20 includes pulsing means 22 for receiving the power and transmitting a series of pulses of power establishing an average power to the pump-motor combination 14 to produce the predetermined volume of fog. The pulsing means 22 includes a switch mode regulator 24 for varying the width of the pulses to control the volume of fog produced by varying the average power supplied to the motor-pump combination 14. The switch mode regulator 24 operates as a pulse width modulator. The switch mode version is utilized in conjunction with the high voltage battery for efficient use of battery capacity. Over 98% of the available battery capacity may be realized, resulting in much smaller and lighter batteries 13. The relatively high battery voltage compared to the required motor running voltage, allows narrow pulses of current to be fed to the motor at a high frequency, e.g., 20 KHz to 100 KHz, and an average current of about 4.5 amperes is maintained. This is the same current the motor 14 would consume when run at a constant voltage of 8.0 volts. By supplying the switch mode regulator 24 with a battery terminal voltage some 50% higher than the desired running voltage, the decrease in terminal voltage of the battery 13 during discharge has little deleterious effect on pump capacity. More particularly, the switch mode regulator 24 is a National LH1605 integrated circuit regulator configured as a buck converter to supply the DC power from the battery 13 with a constant, average voltage of approximately 8.0 volts.

The control means 20 includes feedback means 26 for providing feedback to the switch mode regulator 24 establishing the status of the generating means 18. Feedback is provided by a sensing resistor R1 which, in combination with internal voltage divider resistors within the switch mode regulator 24, will fix the operating voltage at the desired level. Alternatively, the operating voltage of the converter 24 may be determined by a pressure transducer 28 coupled to the compressor 16 outlet. Fully closing the feedback loop around the air compressor by use of the pressure transducer 28 compensates for changes in compressor 16 characteristics with time, such as wear or degradation due to heat or minor leaks. Slight variations in nebulizer head construction can also be taken into account by means of pressure feedback 28. In the preferred embodiment, the switch mode regulator 24 is switchable by a switch means 30 between partial (resistor R1) and full (pressure transducer 28) feedback modes.

The power supply means 12 includes the primary battery power source 13. The internal battery storage cells 13 can not be instantly recharged, so provisions are made to operate the nebulizer compressor 10 on auxiliary power if needed. An adapter cord and plug set 34 may run the assembly from any vehicle with a 12 volt DC electrical system. The adapter 34 is plugged into a cigarette lighter outlet and the selector switch 36 is switched to contact 60 to power the pump-motor 14 from the external power source while also charging the internal battery 13. Switchover may be made automatic with an auxiliary voltage sensing circuit sensing batter 13 voltage and is generally indicated at 37.

Additionally, the power supply means 12 may utilize AC (mains) power supply 38 adapted to power the assembly 10 for nonportable use or charging. The power supply means 12 includes a constant voltage, current limited charger 40 which be used to fully recharge the internal storage battery 13 overnight. Typically, a wall mounted plug-in transformer 42 and voltage regulator 44 provides the 14 volts DC at relatively low current, i.e., 1.5 amperes, necessary to recharge the internal battery 13.

A problem and detraction with all battery operated instrumentation is the general inability to determine remaining operating time on a given charge of the power supply means 12. The assembly 10 includes monitor means 46 for monitoring the charge remaining in the battery 13. The monitor means 46 includes visual indicator means 48 for visually indicating the charge remaining on the battery 13, and audible indicator means 50 for audibly indicating low charge in the battery 13.

The visual indicator means 48 monitors the battery 13 voltage under load by a commercially available bar graph driver 52, an integrated circuit, National LM3914, which provides a stable internal voltage reference and provisions for a ten step L.E.D. output to represent various input voltage levels. The driver 52 is configured in dot mode, and is programmed to present four outputs D1-D4 corresponding to input voltages of 12.6 volts (full charge, green L.E.D. D1), 12.2 volts (normal running, green L.E.D. D2), 11.8 volts (low battery warning, yellow L.E.D. D3), and 10.4 volts (discharged battery-stop, red L.E.D. D4). The intention of the monitor 46 is to provide the user a specific pump-motor 14, compressor 16, nebulizer battery combination 10 a dependable indication of the number of respiratory therapy sessions still available on a given charge of the battery 13. Considering a typical nebulizer use period of nominally 15 to 20 minutes, three sessions would be available until the yellow low battery warning L.E.D. D3 was lit. At that point, only one more session would be available. Use of the device should be terminated when the red (10.4 volt) L.E.D. D4 is lit, so that the battery 13 is not deeply discharged. The recommended end point voltage for sealed lead-acid cells is on the order of 1.66 Volts per cell, while nickel-cadmium cells should not be discharged below 0.9 volts per cell in order to provide maximum longevity.

The audible indicator means 50 is provided whenever the yellow warning L.E.D. D3 or red stop L.E.D. D4 is energized. The yellow level output D3 or pins 12,13 from the driver 82 also drives a logic level inverting PNP transistor Q1 which in turn drives the reset input of a timer integrator circuit 54 Motorola MC1455 configured in classical astable mode. Whenever input pin 4 of the timer 54 is high, the timer 54 begins oscillating. The output of the timer 54 at pin 3 is duty cycle programmed by the resistors R16, R15 and capacitor C9 to be on for one second every 15 seconds or so. An piezo alarm 56 is directly powered by the output, and therefore chirps intermittently to alert the user that the battery 13 is in an incipient discharge state. Further use drops the battery 13 voltage further. At approximately 10.4 volts the red L.E.D. D4 is energized driving a second level inverting PNP transistor Q2 to directly power the piezo alarm 56 through diode D7. The continuous power overrides the pulsed output pin 3 to cause the piezo alarm to sound continuously. The annoying alarm tone should induce the operator to shut off the nebulizer 10 to prevent deep discharge of the battery 13. Infrequent deep discharge cycles are not particularly troublesome, but continuous abuse will materially comprise battery 13 capacity and useful life.

The assembly 10 also includes housing means 58 for supporting and containing the power supply means 12, nebulizer or generating means 18, control means 20, wherein the housing means 58 is portable The housing 58 also contains a fan 59, as commonly known in the art.

The more specific circuitry of the nebulizer assembly 10 is hereinafter described. The charger 40 includes the transformer 42 receiving power from the AC supply 38. The output of the transformer 42 is connected to a rectifier bride 43 which is grounded on its negative output, and its positive output is connected to the voltage regulator 44 (LM7815), wherein a capacitor C1 (470 uF) is connected across the positive and negative terminals of the output of the bridge rectifier 43. The voltage regulator 44 is grounded with a capacitor C2 (10 uF) connected across the output and ground, wherein the output of the voltage regulator 44 is connected through a diode D5 through resistor R2 (5 ohms) to the positive terminal of the battery 13.

The vehicle or external dc adapter 34 has its positive input terminal connected to a first terminal 60 of the power selection switch 36 and to a load resistor R3 to the output of the charger 40 establishing the second terminal 61 of the switch 36. The negative external source 34 terminal is connected to ground. The power selection switch 36 switches between the first terminal 60 and a second terminal 61 and a third terminal 63 which switches battery power 13 on. The switch 36 is connected to the input pin 5 of the switch mode regulator 24, and is connected through L.E.D. D6 through resistor R4 (1K ohm) to ground. A capacitor C3 (100 uF) is connected across the input pin 5 and ground. Pin 4 is connected through capacitor C4 (0.001 uF) to ground, and pin 2 is connected through capacitor C5 (10 uF) to ground. The output pin 8 is connected through coil L1 to the motor 14. The error amplifier input pin 3 is connected to the feedback means 26, which is either the resistor R1 (4.3K ohms) connected to the motor 14 or the pressure transducer 28 sensing the pressure on the air compressor 16. A capacitor C6 (1000 uF) is connected across the terminals of the motor 14.

The monitor 46 includes the visual indicator 48 comprising the driver chip 52 (LM3914). The full charge L.E.D. D1 is connected to pin 10, the normal operating or green L.E.D. D2 is connected to pin 11, the warning or yellow L.E.D. is connected to pins 12 and 13, and the stop or red L.E.D. D4 is connected to pin 14. The input voltage pin 3 is connected through resistor R5 (470 ohm) to the inputs of diodes D1-D4 and to resistor R6 (470 ohms) to ground. Pin 3 is connected to power. Pin 5 is connected to power through resistor R7 (3K ohms), and is connected through resistor R8 (1K ohms) to ground. Pins 4 and 8 are connected through resistor R9 (1.3K ohms) to ground and pin 6 is connected through resistor R10 (820 ohms) to resistor R9, and pin 7 is connector through resistor R11 (100 ohms) to resistor R10. Pins 12 and 13 are connected through resistor R12 (10K ohms) to the base of transistor Q1 (2N3906) having its collector connected through capacitor C7 (0.1 uf) to ground and its emitter connected to the emitter of transistor Q2 (2N3906). Pin 14 is also connected through resistor R13 (10K ohm) to the base of transistor Q2 having its collector connected through diode D7 to the alarm 56. The common emitters are connected to power to pin 8 of the timer 54. The collector of Q1 is connected to pin 4 or the reset pin of the timer 54. The following pin designations refer to timer 54, unless otherwise indicated. Diode D8 is connected through the output pin 3 to the alarm 56. Pin 1 is grounded the control voltage pin 5 is connected through capacitor C8 (0.01 uF) to ground, the discharge pin 7 is connected through resistor R14 (1K ohm) to power, resistor R15 (27K ohms) is to connected through resistor R14 and diode D9 to pins 2 and 6, and a resistor R16 (2M ohms) is connected between pin 7 and to diode D10 to pins 2 and 6. A capacitor C9 (0.22 uF) is connected between pins 2 and 6 and the ground. Capacitor C10 (4.7 uF) is connected across the terminals of the alarm 56.

The invention also includes a method of producing fog. The method includes the steps of supplying electrical current from an electrical power supply means, producing fog in response to said power, and producing a series of pulses of electrical current from the power supply means for establishing an average supply of power to produce a predetermined volume of fog. The method is further characterized by recharging the power supply means with an external power supply, monitoring the charge remaining in the power supply means, visually indicating a predetermined the charge remaining in the power supply means, audibly indicating low charge in the power supply means 13, and varying the widths of the pulses to vary the continuous average power for controlling the volume of the fog produced.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A nebulizer assembly, said assembly comprising: power supply means (12) for supplying power; generating means (18) for producing fog; control means (20) connected between said power supply means (12) and said generating means (18) for switching power to said generating means (18) to produce a predetermined volume of fog; said control means (20) including pulsing means (22) for receiving said power and transmitting a series of pulses of power to said generating means (18) to establish an average power producing said predetermined volume of fog, and feedback means (26) for providing feedback to said pulsing means (22) of the output of said generating means (18).

2. An assembly as set forth in claim 1 further characterized by said power supply means (12) comprising a power storage device (13) for storing said power.

3. An assembly as set forth in claim 2 further characterized by including housing means (58) for supporting said power supply means (12) and said generating means (18) and said control means (20), said housing means (58) being portable.

4. An assembly as set forth in claim 3 further characterized by said control means (20) including charging means (40) for receiving an external power supply and charging said power storage device (13).

5. An assembly as set forth in claim 2 further characterized by said control means (20) including monitor means (46) for monitoring the charge remaining in said power storage device (13) including a charge greater than complete discharge.

6. An assembly as set forth in claim 5 further characterized by said monitor means (46) including visual indicator means (48) for visually indicating the charge remaining in said power storage device (13) including charges of greater than complete discharge while continuing operation of said generating means (18).

7. An assembly as set forth in claim 5 further characterized by said monitor means (46) including audible indicator means (50) for audibly indicating low charge in said power storage device (13) greater than complete discharge.

8. An assembly as set forth in claim 1 further characterized by said pulsing means (22) including modulator means (24) for varying the width of said pulses to control the volume of fog produced by varying said average power.

9. An assembly as set forth in claim 8 further characterized by said generating means (18) including pump and motor (14), and air compressor (16) for producing an output pressure.

10. An assembly as set forth in claim 9 further characterized by said feedback means including pressure transducer (28) at said air compressor (16) for measuring the pressure therein and volume.

11. An assembly as set forth in claim 10 further characterized by said feedback means (26) including a resistor sensing the average power supplied to said motor (14).

12. A method of producing fog, the method including the steps of; supplying electrical current from an electrical power supply means, producing fog in response to said power, producing a series of pulses of electrical current from the power supply means for establishing an average supply of power to produce a predetermined volume of fog, and providing feedback for the production of pulses of the output of the production of fog.

13. A method as set forth in claim 12 further including recharging the power supply means with an external power supply.

14. A method as set forth in claim 12 further including monitoring the charge remaining in the power supply means including a charge greater than complete discharge.

15. A method as set forth in claim 14 further including visually indicating the charge remaining in the power supply means at charges greater than complete discharge.

16. A method as set forth in claim 15 further including audibly indicating a predetermined low charge in the power supply means.

17. A method as set forth in claim 16 further including varying the width of the pulses to vary the continuous average power for controlling the volume of the fog produced.

* * * * *